United States Patent [19]

Tessier et al.

[11] Patent Number: 4,478,850
[45] Date of Patent: Oct. 23, 1984

[54] ESTER

[75] Inventors: Jean Tessier, Vincennes; Jean-Pierre Demoute, Montreuil-sous-Bois, both of France; Werner Bonin, Kelkheim, Fed. Rep. of Germany

[73] Assignee: Roussel Uclaf, Paris, France

[21] Appl. No.: 489,516

[22] Filed: Apr. 28, 1983

[30] Foreign Application Priority Data

Apr. 30, 1982 [FR] France ................... 82 07485

[51] Int. Cl.³ ............... A01N 53/00; C07C 121/75
[52] U.S. Cl. .......................... 424/304; 260/465 D; 424/274; 424/275; 424/285
[58] Field of Search ............ 260/465 D; 424/304, 424/274, 275, 285

[56] References Cited

U.S. PATENT DOCUMENTS 3,666,789  5/1972  Itaya et al. .................. 560/124
3,835,176  9/1974  Matsuo et al. ................ 260/465 D Primary Examiner—Dolph H. Torrence
Attorney, Agent, or Firm—Charles A. Muserlian

[57] ABSTRACT

The novel ester, (S)α-cyano-3-phenoxy-4-fluorobenzyl (1R,cis,Z) 2,2-dimethyl-3-[3-oxo-3-tert.butoxy-propenyl]-cyclopropane-carboxylate, which has the formula

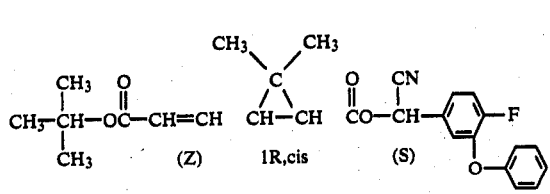

and pesticidal compositions and methods.

14 Claims, No Drawings

ESTER

STATE OF THE ART

Copending U.S. patent application Ser. No. 266,164 filed May 22, 1981, abandoned, describes compounds of the formula

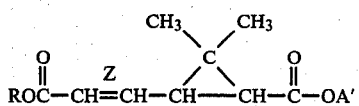

wherein R is optionally unsaturated alkyl or cycloalkyl and A' is a residue of alcohols used in pyrethrinoid synthesis and the double bond has the Z geometry. Also related is copending U.S. patent application Ser. No. 254,537 filed Apr. 15, 1981, Pat. No. 4,402,972.

OBJECTS OF THE INVENTION

It is an object of the invention to provide novel compound A and a process for its preparation.

It is another object of the invention to provide novel pesticidal compositions and a novel method of combatting pests.

These and other objects and advantages of the invention will become obvious from the following detailed description.

THE INVENTION

The novel compound of the invention is (S)α-cyano-3-phenoxy-4-fluoro-benzyl (1R,cis,Z) 2,2-dimethyl-3-[3-oxo-3-tert.butoxy-propenyl]-cyclopropane carboxylate which has excellent pesticidal properties, particularly in the acaricide and ixodicide fields as can be seen from the tests infra.

The novel process of the invention for the preparation of the compound of formula A comprises reacting in an organic solvent (1R,cis,Z) 2,2-dimethyl-3-[3-oxo-3-tert.butoxy-propenyl]-cyclopropane-carboxylic acid or a functional derivative thereof with (S)α-cyano-3-phenoxy-4-fluoro-benzyl alcohol or a functional derivative thereof.

In a preferred mode of the process of the invention, (1R,cis,Z) 2,2-dimethyl-3-[3-oxo-3-tert.butoxy-propenyl] cyclopropane-carboxylic acid is reacted with 1-chloro-N,N-(2-trimethyl)-propenylamine and the resulting product is reacted with (S)α-cyano-3-phenoxy-4-fluoro-benzyl alcohol in the presence of pyridine. The organic solvent is preferably selected from the group consisting of chlorinated aliphatic solvents, aromatic hydrocarbons, aliphatic hydrocarbons and cyclic and non-cyclic ethers.

(1R,cis,Z) 2,2-dimethyl-3-[3-oxo-3-tert.butoxy-propenyl]-cyclopropane-carboxylic acid is described in copending U.S. patent application Ser. No. 266,164 filed May 22, 1981 and the preparation of (S)α-cyano-3-phenoxy-4-fluoro-benzyl alcohol is described in Example 1.

The pesticidal compositions of the invention are comprised of a pesticidally effective amount of the compound of formula A and an inert carrier. The compositions are useful to combat vegetable parasites, parasites in premises and parasites of warm-blooded animals as well as being useful against insects, nematodes and vegetables and animal acarien parasites.

The compositions of the invention have an especially remarkable lethal activity against domestic insects such as houseflies, mosquitoes and cockroaches and a good knock-down effect. They are especially useful to combat insects in the agricultural field such as aphides, lepidoptera larvae and coleoptera larvae and they are usually used at a dose of 10 to 300 g of active ingredient per hectare.

Compound A is very photostable and has a very low toxicity to mammals. All these properties make the compositions useful for modern agrochemistry and permits their use without damage to the environment.

The compositions are equally useful to combat vegetable acariens and vegetable nematodes.

The compositions destined for agrochemical and premises usage may contain more than one active agent and may also contain other pesticides. The said compositions may be in the form of powders, granules, suspensions, emulsions, solutions, aerosol solutions, combustible strips, baits or other classical preparations used for compositions of this nature.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The insecticidal compositions usually contain 0.005 to 10% by weight of the compounds of formula A.

In an advantageous operation for premises use, the compositions are in the form of fumigants. These compositions advantageously have for their inactive portion a combustible serpentine or coil base or an incombustile fibrous substrate in the form of a small plate. In the latter case, the fumigant obtained after incorporation of the active ingredient of formula A is placed in a heating apparatus such as an electromosquitoe destroyer. The usual active dose in this case is 0.03 to 95% by weight.

In the case of a serpentine insecticide, the inert support may be made, for example, of pyrethrum marc, Tabu powder (or Machilus Thumbergii leaf powder), powder of pyrethrum stems, cedar needle powder, sawdust such as pine sawdust, starch and powder of coconut shells. The active dose in this case is preferably 0.03 to 1% by weight.

The compositions of the invention for use in premises may be prepared as a spraying oil containing the active ingredient and the oil may soak the wick of a lamp which is then subjected to combustion. The concentration of the compound of formula A in the oil is preferably 0.03 to 95% by weight.

The insecticidal compositions as well as the acaricidal and nematocidal compositions of the invention may also contain one or more other pesticides and are in the usual powder, granule, suspension, emulsion or solution form. For acaricide use, the compositions are preferably wettable powders for foliar spraying containing 1 to 80% by weight of the active ingredient or liquids for foliar spraying containing 1 to 500 g/l of the acitve ingredient. Also useful are powders for foliar powdering containing 0.5 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

To increase the biological activity of the compositions of the invention, classical synergists may be incorporated therein such as 1-(2,5,8-trioxadodecyl)-2-propyl-4,5-methylenedioxy-benzene (piperonyl butoxide) or N-(2-ethylheptyl)-bicyclo-[2,2-1]-5-heptene-2,3-dicarboximide or piperonyl-bis-2-(2'-n-butoxy-ethoxy)-ethyl acetal (tropital).

The pesticidal compositions of the invention are also useful for combatting animal parasites such as ticks and especially ticks of the Boophilus species, of the Hyalomnia species, of the Amblyomnia species and of the Rhipicephalus species and for combatting all sorts of scabies, especially sarcoptic scabies, psoroptic and chorioptic scabies.

The compositions of the invention show an excellent general tolerance and are equally useful for treating affections created by ticks, lice and scabies.

The said compositions may be administered externally by vaporization, by shampoo, by painting or by bathing. For veterinary usage, the compositions may also be administered by painting the dorsal spine by the "pour on" method as well as being administered digestively or parenterally.

When the compositions are to be used to combat animal parasitic acariens, the active compound of formula A is very often incorporated into alimentary compositions in association with a nutritive mixture adapted to the animal to be fed. The nutritive mixture will vary depending upon the specific animal but usually contains cereals, sugars and grains, soybean press cake, peanuts and turnsole, meal of animal origin such as fish meal, synthetic amino acids, mineral salts, vitamins and antioxidants.

Another feature of the invention are insecticidal acaricidal or nematocidal compositions containing as an active ingredient the compound of formula A and as a second active ingredient at least one pyrethrinoid ester selected from the group consisting of esters of allethrolones, of 3,4, 5,6-tetrahydrophthalimido-methyl alcohol, of 5-benzyl-3-furyl-methyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene methyl)-cyclopropane-carboxylic acids, esters of 3-phenoxy-benzyl alcohol and α-cyano-3-phenoxy-benzyl alcohols with 2,2-dimethyl-3-(2,2-dichlorovinylcyclopropane-1-carboxylic acids, esters of α-cyano-3-phenoxybenzyl alcohols with 2,2-dimethyl-3-(2,2-dibromovinyl)-cyclopropane-1-carboxylic acids, esters of 3-phenoxy-benzyl alcohol with 2-p-chlorophenyl-2-isopropyl-acetic acids, esters of allethrolones, 3,4,5,6-tetrahydrophthalimido-mehtyl alcohol, 5-benzyl-3-furyl-methyl alcohol, 3-phenoxy-benzyl alcohol or α-cyano-3-phenoxy-benzyl alcohols with 2,2-dimethyl-3-(1,2,2,2-tetrahaloethyl)-cyclopropane-1-carboxylic acids where halo is flourine, chlorine or bromine wherein the compounds of formula A and the above pyrethrinoid esters are in all possible stereoisomer forms.

The latter associated compositions of the invention are of particular interest for combatting by the polyvalence of their action a larger range of parasites or by manifesting a synergistic action in some cases.

The novel method of the invention for combatting pests comprises contacting the pest with a pesticidally effective amount of the compound of formula A.

In the following examples there are described several preferred embodiments to illustrate the invention. However, it is to be understood that the invention is not intended to be limited to the specific embodiments.

EXAMPLE 1

(s)α-cyano-3-phenoxy-4-fluoro-benzyl (1R,cis,Z) 2,2-dimethyl -3-[3-oxo-3tert.butoxy-propenyl]-cyclopropane-carboxylate STEP A: (1R,2R, 5S) 6,6-dimethyl-3-oxa-2-[(R) and (S)-α-cyano -3-phenoxy-4-fluoro-benzyloxy]-bicyclo (3,1,0) hexanes A mixture of 16 g of (R,S)α-cyano-3-phenoxy-4-fluoro-benzyl alcohol, 9.4 g of (1,R,2R,5S) 6,6dimethyl-3-oxabicyclo (3,1,0) hexane-2-ol, 100 ml of dichloromethane and 0.1 g of p-toluene sulfonic acid was refluxed for 90 minutes and was then poured into aqueous dilute potassium bicarbonate solution. The decanted organic phase was evaporated to dryness under reduced pressure to obtain 25.06 g of (1R,2R,5S) 6,6-dimethyl-3-oxa-2-[(R,S)α-cyano-3-phenoxy-4-fluoro-benzyloxy]-bicyclo (3,1,0) hexane. The product was chromatographed over silica gel and was eluted with an 8-2 hexane-ether mixture to obtain 8.85 g of the (R) isomer melting at <50° C. and having a specific rotation of $[\alpha]_D^{20} = +102°$ (c=1% in benzene) and then 9.05 g of the (S) isomer melting at 65° C. and having a specific rotation of $[\alpha]_D^{20} = +50°$ (c=0.4% in benzene).

| Circular dichroism (dioxane): | | |
|---|---|---|
| R isomer: | max. at 279 nm | Δε = −0.27 |
| S isomer: | Inflex. at 275 nm | Δε = +0.13 |
| | max. at 281 nm | Δε = +0.15 |

NMR Spectrum (deuterochloroform):

R isomer: Peaks at 1.07 ppm (hydrogens of geminal methyls); at 1.33-1.78 ppm (hydrogens of cyclopropyl); at 3.7-4.1 ppm (hydrogens of —CH$_2$O); at 5.2-5.5 ppm (hydrogen of —OCH—); at 6.9-7.6 ppm (aromatic ring hydrogens)

s isomer: Peaks at 1.0 ppm (hydrogens of geminal methyls); at 1.55-1.57 ppm (hydrogens of cyclopropyl); at 3.8-3.9 ppm and 4.1-4.3 ppm (hydrogens of —CH$_2$O—)at 4.9-5.3 ppm (hydrogen of —OCH); at 6.9-7.6 ppm (aromatic ring hydrogens).

STEP B: (S)α-cyano-3-phenoxy-4-fluoro-benzyl alcohol

A mixture of 9 g of the (S) isomer of Step A, 100 ml of methanol and 90 mg of p-toluene sulfonic acid was stirred at 20° C. for 90 minutes and was then poured into water. The mixture was extracted with chloroform and the organic phase was evaporated to dryness under reduced pressure. The residue was chromatographed over silica gel and eluted with a 7-3 hexane-ethyl acetate mixture containing 1% of acetic acid to obtain 4.5 g of (S)α-cycano-3-phenoxy-4-fluoro-benzyl alcohol with a specific rotation of $[\alpha]_D^{20} = -30°$ (c=0.5% in pyridine).

STEP C: (S)α-cyano-3-phenoxy-4-fluoro-benzyl (1R,cis,Z) 2,2-dimethyl-3-[3oxo-3-tert.butoxy-propenyl]-cyclopropane-carboxylate A solution of 1.45 g of (1R,cis,Z) 2,2-dimethyl -3-[3-oxo-3-tert.butoxy-propenyl]-cyclopropane-carboxylic acid in 5 ml of dichloromethane was progressively added with stirring at 20° C. to a mixture of 1.25 ml of 1-chloro-N,N-(2-trimethylpropenyl)-amine in 10 ml of dichloromethane and the mixture was stirred for 30 minutes. A solution of 1.45 g of the product of Step B, 1.2 ml of pyridine and 10 ml of dichloromethane was slowly added to the mixture and the mixture was then stirred at 20° C. for 18 hours after which water was added followed by an aqueous dilute hydorchloric acid solution. The decanted organic phase was washed with water and evaporated by dryness under reduced pressure. The residue was chromatographed over silica gel and was eluted with a 9-1 hexane-ethyl acetate mixture. The product was crystallized from hexane to obtain 2.04 g of (S)α-cyano-3-phenoxy-4-fluorobenzyl (1R,cis,Z) 2,2-dimethyl-3-[3-oxo-3-tert.butoxy-propenyl]-cyclopropane-carboxylate melting at 114° C. and having a specific rotation of $[\alpha]_D^{20} = +67° \pm 2.5°$ (c=0.5% in chloroform).

NMR Spectrum (deuterochloroform):

Peaks at 1.23–1.27 ppm (hydrogens of geminal methyls); at 1.52 ppm (hydrogens of tert.butyl); at 1.87–2.0 ppm (1-hydrogen of cyclopropyl); at 3.2–3.5 ppm (3-hydrogen of cyclopropyl); at 5.8–6.0 ppm (ethylenic hydrogens α to —COO); at 6.3–6.6 ppm (other ethylenic hydrogens); at 6.35 ppm (hydrogen on carbon attached to —CN); at 6.98 to 7.6 ppm (aromatic hydrogens).

EXAMPLE 2

A soluble concentrate was prepared by homogenously mixing 0.25 g of the compound of Example 1, 1 g of piperonyl butoxide, 0.25 g of Tween 80, 0.1 g of Topanol A (2,4-dimethyl-6-tert.butyl-phenol) and 98.4 g of water.

An emulsifiable concentrate was prepared by intimately mixing 0.015 g of the compound of Example 1, 0.5 g of piperonyl butoxide, 0.1 g of Topanol A, 3.5 g of Tween 80 and 95.885 g of xylene.

An emulsifiable concentrate was prepared by homogenously mixing 1.5 g of the compound of Example 1, 20 g of Tween 80, 0.1 g of Topanol A and 78.4 g of xylene.

A fumigant composition was prepared containing 0.25 g of the product of Example 1, 25 g of tabu powder, 40 g of powdered cedar needles, 33.75 g of powdered pinewood, 0.5 g of brillant green and 0.5 g of para-nitrophenol.

INSECTICIDAL ACTIVITY

A. Knockdown Effect

The knockdown effect of the products against houseflies was determined on 4 day old female houseflies by direct spraying at a concentration of 0.25 g/l in a Kearns and March chamber using as solvent a mixture of 5% acetone and 95% of Isopar L (petroleum solvent) and using 2 ml of solution per second.

50 insects were used for each test and the readings were taken every minute for 10 minutes and then at 15 minutes to determine the $KT_{50}$ value which was 3.8 minutes for the compound of Example 1.

B. Lethal Activity

The lethal activity was determined on female houseflies 4 to 5 days old and each received a topical application of 1 μl of an acetone solution of the compound of Example 1 on the dorsal thorax with an Arnold micromanipulator. 50 insects were used for each test and the number of dead insects after 24 hours was used to calculate the $DL_{50}$ in nanograms per individual to kill 50% of the insects. The $DL_{50}$ was 1.8 ng per individual.

C. Lethal Activity on Cockroaches

Films were prepared by depositing with a pipette an acetone solution of different concentrations of the compound of Example 1 on the bottom of a glass Petri dish whose edges were previously treated with talc to prevent the escape of the insects which were placed in the dish. The lethal concentration ($CL_{50}$) was determined to be 0.087 mg/m$^2$.

D. Lethal Activity on Acanthoscelides Obtectus

The test was effected by topical application of an acetone solution with an Arnold micromanipulator and after treatment, the adult individuals were placed in a natural medium. The number of dead 48 hours after treatment was used to calculate the $DL_{50}$ which was 8.3 mg per individual.

E. Lethal Effect on *Aphis cracivora*

The test was effected on young adults 2 to 3 days old and 10 individuals were used for each test concentration. Bean leaves were sprayed with a toxic solution using Fisher pistol and the bean leaf was placed in a Petri box made of plastic material with a ring of humidified paper. The treatment was effected with 2 ml of a mixture of water, acetone and the compound of Example 1 using 1 ml per leaf face. The leaf was infested with the insects after the leaf was dried and the contact-ingestion test lasted one hour. Then, the insects were placed on non-treated leaves. The number of dead insects was determined after 24 hours and gave a $DL_{50}$ of 5.2 mg/l.

The above tests show that the compound of Example 1 has a very good insecticidal activity and an excellent knock-down effect.

F. Acaricidal Activity

Bean plants with 2 leaves were infested with 25 female Tetranychus urticae per leaf and were placed in an airy place with a lighted ceiling with constant light. The plants were treated with a Fischer pistol with 4 ml of a toxic solution per plant in a 1—1 mixture of water and acetone. The plants were dried for 12 hours and were then infested. The number of dead was determined 80 hours later and the dosage rate was 5 g per hectoliter. The compound of Example 1 had a $CL_{50}$ of 536 mg/hl which was an excellent acaricidal activity.

G. Ixodicidal Activity a. Against *Boophilus Microplus* Larvae

The compound of Example 1 was dissolved in a mixture of 50 g of phenylsulfonate CA 70, 70 g of Emulsogen EL 360 and 780 g of Isophoron to obtain a 10% emusifiable concentrate which was diluted with water to obtain a solution with a concentration of 10 ppm, 1 ppm and 0.1 ppm of active compound.

Using a revolving sprayer, the different solutions were sprayed on larvae of tropical beef ticks of Boophilus microplus (Mexican strain sensitive and DDT resistant) and the number of dead and live larvae counted after 24 hours to determine th percentage of mortality and in all instances, the percentage was 100%.

b. Against Adult *Rhipicephalus Appendiculatus* and *Ambloymnia hebraeum*

As in test a, 10 of the said ticks were sprayed at concentrations of 100, 10 and 1 ppm of the compound of Example 1 and the percentage of mortality was 100% in each test.

c. Inhibition of Reproduction of *Boophilus microplus* Ticks

Female *Boophilus Microplus* (sensible Mexican strain) about to lay eggs were dipped for 5 minutes into a solution prepared as in test a and then were placed in an heated enclosure for the egg laying. The percentage of ticks not laying 2 weeks after treatment and the amount of eggs laid two weeks as compared to controls and the percentage of larvae being hatched after 3 weeks were determined to calculate as a function of the obtained numbers the inhibition of reproduction with 100% being total inhibition and 0% being identical to the controls. At a dose of 0.19 ppm, the percentage of inhibition for the compound of Example 1 was 100%.

The said tests show that the tested compound has a very good tickicidal activity.

Various modifications of the compounds and methods of the invention may be made without departing from the spirit or scope thereof and it should be understood that the invention is intended to be limited only as defined in the appended claims.

What we claim is:

1. (S)α-cayano-3-phenoxy-4-fluoro-benzyl (1R,cis,Z) 2,2-dimethyl-3-[3-oxo-3-tert.butoxy-phenyl]-cyclopropanecarboxylate.

2. A pesticidal composition comprising a pesticidally effective amount of the compound of claim 1 and a pesticidal carrier.

3. A composition of claim 2 comprising as a second active ingredient at least one pyrethrinoid ester selected from the group consisting of esters of allethrolone, 3,4,5,6-tetrahydrophthalimino-methyl alcohol, of 5-benzyl-3-furylmethyl alcohol, of 3-phenoxy-benzyl alcohol and α-cyano-3-phenoxy-benzyl alcohols with chrysanthemic acids, esters of 5-benzyl-3-furyl- methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxy-benzyl alcohols and 2,2-dimethyl-3-(2,2-dichlorovinyl)cyclopropane-1-carboxylic acids, esters of α-cyano-3-phenoxybenzyl alcohols and 2,2-dimethyl-3-(2,2-dibromovinyl)-cyclopropane-1-carboxylic acids, esters of 3-phenoxy-benzyl alcohol and 2-p-chlorophenyl-2-isopropyl-acetic acids, esters of allethrolone, 3,4,5,6-tetrahydrophthalimido-methyl alcohol, 5-benzyl-3-furylmethyl alcohol, 3-phenoxy-benzyl alcohol or α-cyano-3-phenoxy-benzyl alcohols and 2,2-dimethyl-3-(1,2,2,2-tetrahaloethyl)-cyclopropane-1-carboxylic acids where halo is fluorine, chlorine and bromine wherein the said second compounds are in all possible stereoisomer forms of the acids and alcohols of the pyrethrinoid esters.

4. A nematocidal composition comprising a nematocidally effective amount of the compound of claim 1 and a inert carrier.

5. An acaricidal composition comprising an acaricidally effective amount of the compound of claim 1 and an inert carrier.

6. An insecticidal composition comprising an insecticidally effective amount of the compound of claim 1 and an inert carrier.

7. An ixodicidal composition comprising an ixodicidally effective amount of the compound of claim 1 and an inert carrier.

8. A feed composition for warm-blooded animals containing an acaricidally effective amount of the compound of claim 1.

9. A method of combatting insects, nematodes and acarien pests of vegetables, premises and warm-blooded animals comprising contacting the insects, nematodes or acarien pests with a effective amount of the claim 1.

10. A method of combatting insects comprising contacting insects with an insecticidally effective amount of the compound of claim 1.

11. A method of combatting nematodes comprising contacting nematodes with a nematocidally effective amount of the compound of claim 1.

12. A method of combatting acariens comprising contacting acariens with an acaricidally effective amount of the compound of claim 1.

13. A method of combatting ixodes comprising contacting ixodes with an ixodicidally effective amount of the compound of claim 1.

14. The method of claim 9 wherein there is used as a second active ingredient at least one pyrethrinoid ester selected from the group consisting of esters of allethrolone, of 3,4,5,6-tetrahydrophthalimino-methyl alcohol, of 5-benzyl-3-furyl-methyl alcohol, of 3-phenoxy-benzyl alcohol and α-cyano -3-phenoxy-benzyl alcohols with chrysanthemic acids, esters of 5-benzyl-3-furyl methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxy-benzyl alcohols and 2,2-dimethyl-3-(2,2-dichlorovinyl)cyclopropane-1-carboxylic acids, esters of α-cyano-3-phenoxybenzyl alcohols and 2,2-dimethyl-3-(2,2-dibromovinyl)-cyclopropane-1-carboxylic acids, esters of 3-phenoxy-benzyl alcohol and 2-p-chlorophenyl-2-isopropyl-acetic acids, esters of allethrolone, 3,4,5,6-tetrahydrophthalimido-methyl alcohol, 5-benzyl-3-fury-methyl-alcohol, 3-phenoxy-benzyl alcohol or -cyclo-3-phenoxy-benzyl alcohols and 2,2-dimethyl-3-(1,2,2,2-tetrahaloethyl)-cyclopropane-1-carboxylic acids where halo is fluorine, chlorine and bromine wherein the said compound of second are in all possible stereoisomer forms of the acids and alcohols of the pyrethrinoid esters.

\* \* \* \* \*